US009791682B2

(12) United States Patent
Schanne-Klein et al.

(10) Patent No.: US 9,791,682 B2
(45) Date of Patent: Oct. 17, 2017

(54) QUANTITATIVE NONLINEAR OPTICAL MICROSCOPY USING A SHAPED BEAM

(71) Applicants: ECOLE POLYTECHNIQUE, Palaiseau (FR); CENTRE NATIONAL DE LA RECHERCHE SCIENTIFIQUE, Paris (FR)

(72) Inventors: Marie-Claire Schanne-Klein, Verrieres le Buisson (FR); Emmanuel Jean-Marc Beaurepaire, Palaiseau (FR); Mathias Strupler, Montreal (CA); Delphine Debarre, Paris (FR); Nicolas Olivier, Belfort (FR); Pierre Mahou, Bures-sur-Yvette (FR)

(73) Assignees: ECOLE POLYTECHNIQUE, Palaiseau (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 596 days.

(21) Appl. No.: 14/366,809

(22) PCT Filed: Dec. 3, 2012

(86) PCT No.: PCT/FR2012/052784
§ 371 (c)(1),
(2) Date: Jul. 30, 2014

(87) PCT Pub. No.: WO2013/093275
PCT Pub. Date: Jun. 27, 2013

(65) Prior Publication Data
US 2014/0347462 A1    Nov. 27, 2014

(30) Foreign Application Priority Data
Dec. 20, 2011  (FR) ...................................... 11 62056

(51) Int. Cl.
G02B 21/06  (2006.01)
G02B 21/36  (2006.01)
(Continued)

(52) U.S. Cl.
CPC ......... *G02B 21/06* (2013.01); *G01N 21/6486* (2013.01); *G01N 21/65* (2013.01);
(Continued)

(58) Field of Classification Search
None
See application file for complete search history.

(56) References Cited

U.S. PATENT DOCUMENTS 7,194,118 B1    3/2007  Harris et al.
2001/0045529 A1* 11/2001  Iketaki .................. G01J 3/4406
250/493.1
(Continued)

FOREIGN PATENT DOCUMENTS

EP  0627643  12/1994
JP  H0815156 A  1/1996
(Continued)

OTHER PUBLICATIONS

Botcherby et al., "Scanning two photon fluorescence microscopy with extended depth of field," Optics Communications (2006), vol. 268, pp. 253-260.
(Continued)

*Primary Examiner* — Andy Rao
*Assistant Examiner* — Tyler Edwards
(74) *Attorney, Agent, or Firm* — Greer, Burns & Crain, Ltd.

(57) ABSTRACT

A nonlinear optical microscope is provided, including source of a pulsed laser beam; a spatial light modulator for modulating the spatial profile of the pulsed laser beam; an objective for guiding the modulated beam towards a slide
(Continued)

intended to carry a specimen; and a detector for collecting signals originating from the specimen, wherein the spatial light modulator is designed to modulate the intensity and/or the phase of the pulsed laser beam on the rear pupil of the objective to produce a beam that is axially extended and confined in one or two lateral directions after focusing by the objective, and wherein the slide is placed on a motorized stage of a histology slide scanner assembly.

13 Claims, 2 Drawing Sheets

(51) Int. Cl.
*G01N 21/64* (2006.01)
*G01N 21/65* (2006.01)
*G02B 21/26* (2006.01)
*G01N 33/483* (2006.01)
*G02B 21/00* (2006.01)

(52) U.S. Cl.
CPC ....... *G01N 33/4833* (2013.01); *G02B 21/004* (2013.01); *G02B 21/0032* (2013.01); *G02B 21/0076* (2013.01); *G02B 21/26* (2013.01); *G02B 21/365* (2013.01); *G01N 2021/653* (2013.01); *G01N 2201/0697* (2013.01)

(56) References Cited

U.S. PATENT DOCUMENTS

| | | |
|---|---|---|
| 2003/0231791 A1 | 12/2003 | Torre-Bueno et al. |
| 2005/0258375 A1 | 11/2005 | Mertz et al. |
| 2010/0150472 A1 | 6/2010 | Chen |
| 2010/0187208 A1* | 7/2010 | Dantus ............. G01J 11/00 219/121.72 |
| 2010/0188496 A1* | 7/2010 | Xie ............. G01J 3/10 348/79 |
| 2010/0253774 A1 | 10/2010 | Yoshioka et al. |
| 2011/0174986 A1 | 7/2011 | Kempe et al. |

FOREIGN PATENT DOCUMENTS

| | | |
|---|---|---|
| JP | 2006113484 | 4/2006 |
| WO | 0135325 | 5/2001 |
| WO | 2012127880 A1 | 9/2012 |

OTHER PUBLICATIONS

Dufour et al., "Two-photon excitation fluorescence microscopy with a high depth of field using an axicon," Applied Optics (2006), 45(36), pp. 9246-9252.

Novotny et al., "Principles of Nano-Optics (Chapters 1-5)," (2006), pp. 1-182.

Olivier et al., "Two-photon microscopy with simultaneous standard and extended depth of field using a tunable acoustic gradient-index lens," Optics Letters (2009), 34(11), pp. 1684-1686.

Planchon et al., "Rapid three-dimensional isotropic imaging of living cells using Bessel beam plane illumination," Nature Methods (2011), 8(5), pp. 417-423.

Japanese Office Action for Japanese Patent Application No. 2014-548137 dated Sep. 27, 2016.

* cited by examiner

QUANTITATIVE NONLINEAR OPTICAL MICROSCOPY USING A SHAPED BEAM

BACKGROUND

The present invention relates to a nonlinear or multiphoton optical microscope equipped for the performance of imaging with good lateral resolution. It can be applied with particular benefit, but non-limitatively, to the quantitative imaging of collagen or of lipid content.

Generally, image resolution in nonlinear optical microscopy is linked to the square or the cube of the exciting intensity distribution. The usual nonlinear optical microscopes use a Gaussian-type excitation profile which is the natural distribution obtained with a non-shaped laser beam (Gaussian intensity profile and flat phase at the input to the focusing objective). The resolution is then from 300-400 nm in the lateral direction and from 1-3 microns in the axial direction, under usual conditions of excitation and detection (numerical aperture close to 1, excitation wavelength close to 1 µm). This good axial resolution is equivalent to a shallow depth of field and does not allow imaging in one go of a thin tissue section the thickness of which is a few microns (typically 2-7 µm). The larger the imaged field, the more critical this becomes. It is often essential, in particular in histology, to image large areas of interest (typically on the scale of centimeters) by moving the specimen and reconstituting a mosaic of images thereof. The imaged area must then remain flat and horizontal at the scale of this axial resolution of a few microns for the section to be imaged correctly. In practice this is never the case as microscope slides are not flat on this scale, the sections are never perfectly laid out, and it is very difficult to align the slide parallel to the focal plane within a few microns over distances of the order of a centimeter. FIGS. 2a and 2b show multiphoton imaging of a thin tissue section (typically 5 µm thick) having defects of flatness or of horizontality. FIG. 2a is according to the prior art and relates to the use of a strongly focused Gaussian beam (numerical aperture>0.5): the lateral resolution is satisfactory, but the depth of field is less than the thickness of the section and, as a result, the imaged volume sometimes extends beyond the tissue. FIG. 2b is according to the prior art and relates to the use of a weakly focused Gaussian beam (numerical aperture>0.5): the depth of field is greater, which makes it possible to keep the imaged volume within the tissue, but the lateral resolution is severely degraded.

Moreover, publications are known in the literature teaching the use of Bessel beams for extending the depth of field while retaining the good lateral resolution of an excitation beam. Among these publications, the following are distinguished:

"Two-photon excitation fluorescence microscopy with a high depth of field using an axicon"; Pascal Dufour et al., Applied Optics/vol. 45, No. 36/20 Dec. 2006;

"Scanning two photon fluorescence microscopy with extended depth of field"; E. J. Botcherby et al., Optics Communications 268 (2006) 253-260;

"Rapid three-dimensional isotropic imaging of living cells using Bessel beam plane illumination"; Thomas A Planchon et al., Nature Methods/vol. 8 No. 5/May 2011; and "Two-photon microscopy with simultaneous standard and extended depth of field using a tunable acoustic gradient-index lens"; Nicolas Olivier et al., Optics Letters/vol. 34, No. 11/Jun. 1, 2009.

SUMMARY

The aim of the present invention is to achieve imaging with good lateral resolution in particular on slides that do not have perfect flatness and horizontality.

Another aim of the invention is to propose an imaging system of high sensitivity and specificity. Yet another aim of the present invention is an imaging system capable of rapidly acquiring large areas of interest.

At least one of the aforementioned objectives is achieved with a nonlinear optical microscope comprising:
- a source of a pulsed laser beam,
- spatial light modulator for modulating the spatial profile of the pulsed laser beam,
- an objective for guiding the modulated beam towards a slide intended to carry a specimen, and
- detection means for collecting signals originating from the specimen.

According to the invention, the spatial light modulator is designed to modulate the intensity and/or the phase of the pulsed laser beam on the rear pupil of the objective so as to produce a beam that is axially extended and confined in one or two lateral directions after focusing by the objective. Moreover, the slide is placed on a motorized stage of a histology slide scanner assembly.

The device thus defined can be considered as an intelligent combination of a slide scanner and a nonlinear microscope, this combination being obtained by a particular arrangement of different components in relation to each other.

The beams produced can be intermediate beams between Gaussian beams and Bessel beams. Such beams can in particular be generated based on the teaching of the publication "Principles of nano-optics", L. Novotny and B. Hecht, Cambridge Univ. Press, 2006, in particular Chapters 1 to 5 for the spatial shaping of beams.

However, the modulated beam is preferably a Bessel beam produced in the form of an annular intensity distribution on the rear pupil of the objective.

According to the invention, the slide scanner assembly can comprise:
- a source of white light,
- a condenser for guiding the white light towards the slide, and
- a camera for producing an image from the light originating from the slide.

Preferably, an integrated or remote processing unit is provided for retrieving the signals originating from the detector and reconstructing the multiphoton images, so as to associate them with conventional images originating from the camera. The two images are reset and combined automatically, after a step of calibration on model specimens.

With the microscope according to the invention, it is henceforth possible, in particular in histology, to image large areas of interest, typically on a scale of centimeters, by moving the slide holding the specimen and by reconstituting a mosaic of images. This movement is in particular obtained by driving the stage and therefore the slide with a sweeping motion. The slide is placed on the motorized stage with automatic slide loading. Each slide holds a specimen for analysis. The stage is motorized in two dimensions so that the entire surface of the slide can be swept. The stage can also be motorized in the axial direction in addition to or instead of the motorized axial displacement of the objective. Preferably, in order to further limit the duration of acquisition while retaining a good resolution, several digital images of different separate parts of the slide can be acquired. These images then make it possible to reconstitute a single image of the whole of the slide or of different regions of interest of the specimen.

Advantageously, the invention relates to the implementation of nonlinear or multiphoton optical imagery based on the use of shaped beams, in particular the beams known as Bessel beams, for the excitation of the nonlinear optical processes in multiphoton microscopy. The excitation volume obtained by a Bessel beam is extended in the axial direction with respect to that obtained with a conventional Gaussian beam, but has a similar lateral resolution. The excitation volume thus adopts the form of a tube the length of which is adjustable from a few microns to several hundred microns. The microscope according to the invention based on this type of excitation therefore makes it possible to image in one go systems having a thickness of up to several hundred micrometers with a sub-micrometric lateral resolution, in a robust manner within scattering media.

More generally, the beam shaping can be adapted to the specificities of the specimens investigated by adjusting the intensity and phase distribution on the rear pupil of the objective. Thus a beam is produced that is extended axially and confined in one or two lateral directions after focusing by the objective.

The use of a multipoint system can complement this type of shaping. Several beams that are extended axially and confined laterally are thus sent simultaneously to the slide, and the point detector is replaced by a camera.

According to an advantageous feature of the invention, the detection means comprise a condenser and a detector arranged downstream of the slide with respect to the propagation of the pulsed laser beam so as to detect transmission signals. The condenser can be the condenser used for guiding the incoherent light source towards the slide. It can be replaced by an objective having a high numerical aperture.

It can also be provided for the detection means to comprise a detector, in particular in addition to the detector for the transmission, arranged so as to detect signals emitted rearwards or reflected from the slide by means of the objective used for the excitation. To this end, a dichroic filter can be used in the optical path of the laser beam upstream of the slide so as to direct the reflected signals towards this detector.

Preferably, the objective and the condenser are respectively arranged on either side of the slide. For example, the light of the slide scanner can illuminate the underside of the slide while the laser beam reaches the top side of the slide where the specimen is located. If the pulsed laser beam for the multiphoton excitation and the light source for the slide scanner are arranged on the same side of the specimen, the objective used for guiding the Bessel beam is used for guiding the light towards the slide instead of the condenser. A second objective is then placed on the other side of the specimen for collecting the transmitted light and guiding it towards the camera. The "slide scanner" assembly can also be reduced to the slide support with motorized displacement and automatic loading, without transmitted light visualization. In other words, either the white light visualization can be dispensed with, i.e. retaining only the motorized stage and the automatic loading of the slide scanner, or placing the multiphoton and white light systems on the same side by using two objectives. The two latter solutions are less practical.

According to an advantageous feature of the invention, the objective has a numerical aperture above 0.5 so as to strongly focus the Bessel beam and obtain a very satisfactory lateral resolution.

Preferably, the pulsed laser beam is a femtosecond pulse train, for example around 100 fs with a repetition rate greater than approximately ten MHz, for example around 100 MHz, and a power of several hundred milliwatts. Generally, a laser beam is used that is capable of generating the expected nonlinear phenomena depending on the specimen to be analyzed. In particular, media are used in which second harmonic generation (SHG) or third harmonic generation (THG), two-photon excited fluorescence (2PEF), coherent anti-Stokes Raman scattering (CARS), stimulated Raman scattering (SRS), four-wave mixing (FWM), or other coherent or incoherent nonlinear optical contrasts are utilized.

According to an advantageous feature of the invention, the spatial light modulator comprises an element allowing the shaping of the Bessel beam. This element can in particular be chosen from:
    an axicon or conical lens;
    a diffractive element;
    a liquid crystal modulator; and
    a modulable liquid lens of the acoustic type.

Preferably, means of driving the laser beam with a sweeping motion are also provided. This sweeping takes place in one plane and can additionally be provided with an axial displacement of the objective so as to produce images in 3D. These sweeping means can comprise galvanometric, piezoelectric, or other elements, displacing the laser source, and/or integrated in one of the elements passed through by the laser beam and/or integrated in an additional optical element placed in the optical path of the laser beam. The combination of the sweeping motion of the laser beam with the sweeping motion of the motorized stage makes it possible to obtain accurate images having a high resolution and of different areas of interest.

According to another aspect of the invention, there is proposed at least one of the following applications implementing the microscope according to the invention:
    application to the quantitative imaging of collagen by using the intrinsic second harmonic generation (SHG) signal of fibrillar collagen;
    application to quantitative imaging of the lipid content of a tissue by using a signal of the third harmonic generation (THG), coherent anti-Stokes Raman scattering (CARS), stimulated Raman scattering (SRS) and/or four wave mixing (FWM) type, and
    application to cellular or extra-cellular quantitative imaging, such as for example elastin, by using a two- or three-photon excited fluorescence signal.

In other words, such a device can in particular be applied to the quantitative imaging of collagen in unstained biopsies by using the intrinsic SHG signal of fibrillar collagen. It makes it possible to measure quantitatively the accumulation of fibrillar collagen on large areas of interest of a tissue by at the same time overcoming the problems of flatness and of horizontality of the histology slide.

It has been demonstrated that SHG microscopy is a structural probe of the fibrillar organization of collagen. It is essential to quantify the accumulation of fibrillar collagen in numerous pathologies associated with tissue remodelling. This is the case for example of the fibrogenic pathologies (fibroses of the liver, kidney, lung) including chronic implant diseases. It has thus been shown that the accumulation of fibrillar collagen makes it possible to diagnose undesirable development of these pathologies. More generally, it is useful to quantify the presence of fibrillar collagen in tissue remodelling as a whole, whether of immunological, cancerous, infectious origin, etc.

The benefit of SHG microscopy in this context resides in the fact that it is very specific to fibrillar collagens while not requiring staining or marking, which ensures excellent reproducibility. This is a decisive advantage for carrying out multi-centre research for the evaluation of new treatments or for fundamental research. But the accumulation of fibrillar collagen is in general extremely heterogeneous in the affected organs and requires the imaging of large areas of interest (at least on the scale of centimeters). The device of the invention makes it possible to carry this out while retaining a sub-micrometric lateral resolution which maintains a good sensitivity for the detection of small fibrils of collagen. Thus the extent of the network of fibrillar collagen is measured quantitatively over a large area of interest by acquiring a single image in the axial direction, i.e. much more quickly and directly than with Gaussian beams, for which it is necessary to acquire a stack of several images in the axial direction. The invention could moreover make it possible to exploit the intensity of the SHG signal for quantitatively measuring the number of collagen fibrils aligned in parallel in the focal volume. This would necessitate generating models of the construction of coherent signals with shaped beams taking account of the phase variation of the excitation signal along the focal volume.

Such a microscope for SHG signalling thus allows a quantitative diagnosis of fibrogenic pathologies or any pathology involving the accumulation of fibrillar collagen.

Similarly, the device of the invention can serve to rapidly characterize the number and size of the lipid droplets present in a tissue section or even a small organism (of the *c elegans* type) by third harmonic generation (THG) microscopy or coherent Raman microscopy (CARS, SRS, etc.). These techniques do not require staining or marking, which greatly improves the reproducibility of the measurements.

BRIEF DESCRIPTION OF THE DRAWINGS

Other advantages and features of the invention will become apparent on examination of the detailed description of an embodiment which is in no way limitative, and the attached drawings, in which:

FIG. 2*a* relates to the use of a strongly focused Gaussian beam according to the prior art, it is noted that the depth of field is less than the thickness of the tissue; the focal volume is situated entirely within the tissue or may fall outside it due to defects of flatness or horizontality;

FIG. 2*b* relates to the use of a weakly focused Gaussian beam according to the prior art, a large focal volume is noted, corresponding to a weak lateral resolution, and covering the entire thickness of the tissue;

FIG. 2*c* relates to the use of a strongly focused Bessel beam according to the present invention, a fine focal volume is noted, in the form of a tube, corresponding to a high lateral resolution, and covering the entire thickness of the tissue even in the event of a defect in flatness and horizontality;

FIG. 3*a* relates to the use of a strongly focused Gaussian beam according to the prior art; FIG. 3*b* relates to the use of a strongly focused Bessel beam according to the present invention;

DETAILED DESCRIPTION

Figure 1:
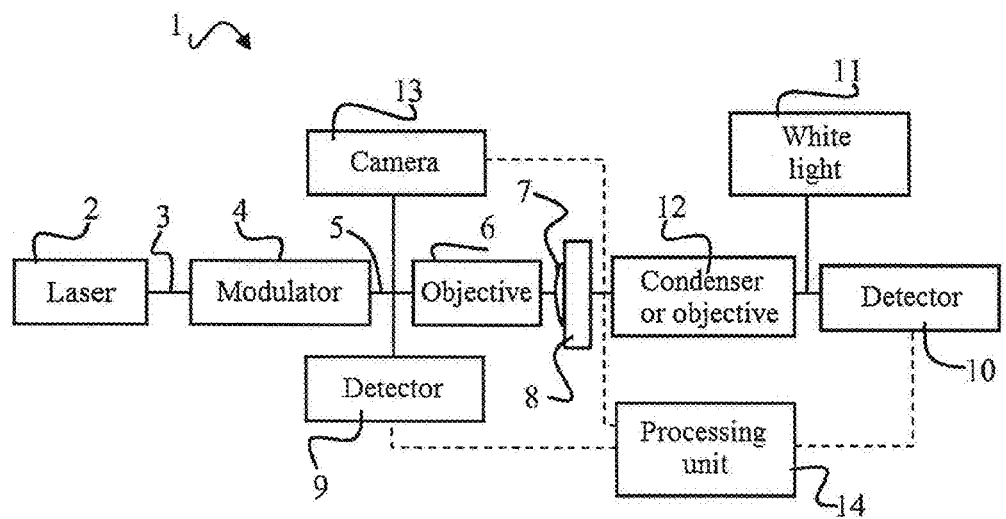
FIG. 1 is a diagrammatic view of a device according to the invention.

With reference to FIG. 1, a device 1 according to the invention can be seen, comprising a laser source 2 emitting an excitation beam 3, such as for example a femtosecond-pulsed laser. This laser source 2 can be adjustable, in particular in intensity or temporally (spectral width, duration, rate and spectral phase of the pulses, etc). By way of example, this is a pulsed laser beam delivering pulses of approximately 100 fs, with a repetition rate of 100 MHz and an average power of a few hundred milliwatts.

The excitation beam 3 is spatially shaped by a spatial light modulator 4. This modulator can comprise an axicon or a conical lens, a diffractive element, a liquid-crystal modulator, an acoustic liquid lens or any other spatial light modulator capable of performing a Bessel-type shaping.

The present invention makes explicit reference to the following publications, which provide more detailed information relating to the generation of a Bessel beam:

"*Two-photon excitation fluorescence microscopy with a high depth of field using an axicon*"; Pascal Dufour et al., Applied Optics/vol. 45, No. 36/20 Dec. 2006; this publication teaches the use of an axicon;

"*Scanning two photon fluorescence microscopy with extended depth of field*"; E. J. Botcherby et al., Optics Communications 268 (2006) 253-260; a diffractive element is used to provide an annular illumination and to generate a Bessel beam;

"*Rapid three-dimensional isotropic imaging of living cells using Bessel beam plane illumination*"; Thomas A Planchon et al., Nature Methods vol. 8 No. 5/May 2011; here orthogonal geometry is used; and "*Two-photon microscopy with simultaneous standard and extended depth of field using a tunable acoustic gradient-index lens*"; Nicolas Olivier et al., Optics Letters/vol. 34, No. 11/Jun. 1, 2009; in this publication an acousto-optic lens is used.

The elements disclosed in these publications are incorporated into the present invention insofar as these elements are not incompatible with the teaching of the present invention.

At the input to the objective 6, the Bessel beam 5 has an average intensity distribution in the form of a ring. A ring of light is formed on the rear pupil of the objective 6. The Bessel beam is then focused on a specimen 7 placed on the slide 8. This Bessel beam has an extended depth of field. The nonlinear signals originating from the specimen 7 are captured on reflection, or by epidetection, by the detector 9 and/or on transmission by the detector 10. The present invention is in particular remarkable for the fact that the nonlinear optical microscopy elements that have just been described are combined with a histology slide scanner comprising a source of while light 11 illuminating an objective or a condenser 12. This white light is then guided towards the specimen 7 through the slide 8. The digital camera 13 makes it possible to capture digital images of the specimen from the white light originating from the specimen.

A processing unit 14 is provided, equipped with the necessary software and hardware means known to a person skilled in the art for driving different components of the device 1 according to the invention, processing the digital images from the digital camera 13 and the signals originating from the detectors 9 and/or 10, then displaying images on a screen.

The slide 8 is carried by a motorized stage with automatic loading. The acquisition of an image is obtained by a sweeping motion of the motorized stage.

The device according to the invention can comprise sweeping means (not shown), which make it possible to laterally sweep the specimen with the Bessel beam 5 output from the spatial light modulator 4. These sweeping means can comprise for example non-resonant mirror scanners and/or acousto-optic elements between the modulator and the objective. They are advantageously controlled in combination with the sweep control of the motorized stage.

Figure 2:
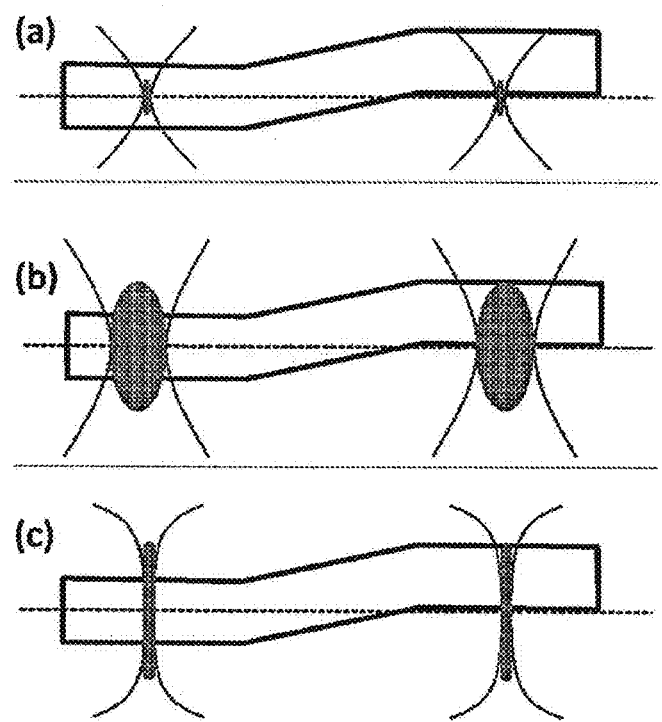
FIGS. 2*a* to 2*c* are diagrammatic views of multiphoton images of a thin tissue section, typically 5 µm thick, having defects of flatness or horizontality.

In FIG. 2c, a multiphoton image is seen of a thin tissue section, typically 5 µm in thickness, having defects of flatness or of horizontality. It is noted that a strongly focused Bessel beam, with a numerical aperture above 0.5, allows a satisfactory lateral resolution, and a depth of field greater than the thickness of the section, making it possible to overcome any defect of flatness.

One of the advantages of the device according to the present invention is the rapidity with which images can be obtained. The use of these Bessel beams in multiphoton microscopy allows an image to be obtained in a single acquisition, for the following reasons:

(i) the extended excitation volume in the axial direction makes it possible to probe a section of a few micrometers in thickness in its entirety, even over large regions of interest having defects of flatness or of horizontality (see FIG. 2c);

(ii) the lateral resolution is kept at a level similar to that obtained with Gaussian beams, allowing a good sensitivity at a sub-micrometric scale; this is not possible if less focused Gaussian beams are used as in FIG. 2b of the prior art;

(iii) the signal level obtained in each plane is not significantly reduced by the axial extension of the excitation volume because the excitation intensity in each plane is not reduced.

Figure 3:
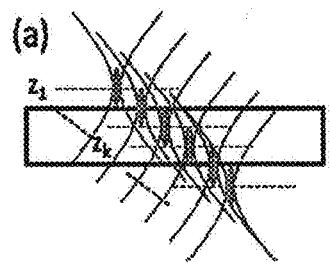
FIGS. 3*a* and 3*b* are diagrammatic views of multiphoton images of a thin section of tissue or of a cell, typically of a few µm in thickness.
Figure 3:
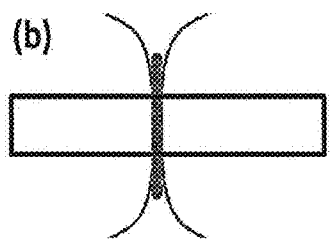

FIGS. 3a and 3b show diagrammatic views of the point spread function (PSF) for multiphoton imaging of a thin section of tissue or of a cell, typically of a few µm in thickness, with a good lateral resolution (numerical aperture>0.5). The point spread function for a Gaussian beam according to the prior art is shown in FIG. 3a.

It is necessary to calculate the contributions of several axially shifted images according to the following equation:

$$I_{NL} = \sum_{k=1}^{p} I_{NL}(z_k) = \sum_{k=1}^{p} \left| \int_{z_k} \chi^{(n)}(z) E_{\omega}^n(z) e^{ni\varphi(z)} dz \right|^2$$

Where $I_{NL}$ is the intensity of the nonlinear optical signal over the entire thickness of the specimen, $I_{NL}(z_k)$ is the intensity of the nonlinear optical signal detected when the excitation beam is focused to the depth $z_k$ where k varies from 1 to p, $\chi^{(n)}(z)$ is the effective nonlinear optical susceptibility of order n at the depth z, $E_{\omega}^n(z)$ is the amplitude of the electrical excitation field of frequency ω at the depth z, raised to the power n, $\varphi(z)$ is the phase of the electrical excitation field of frequency ω at the depth z and $$\int_{z_k}$$

corresponds to the integral over the focused excitation volume at the depth $z_k$. n is an integer for example between 2 and 4, for example 2 for SHG, 3 for THG, CARS, SRS, 2PEF, and 4 for 3PEF.

When a Bessel beam is used, only one image is necessary because the beam is so far extended axially that it goes beyond the thickness of the tissue while retaining an excellent lateral resolution as can be seen in FIG. 3b. A single contribution according to the following equation is necessary:

$$I_{NL} = \left| \int \chi^{(n)}(z) E_{\omega}^n(z) e^{ni\varphi(z)} dz \right|^2$$

Where the integral is carried out over the total thickness of the specimen.

Figure 4:
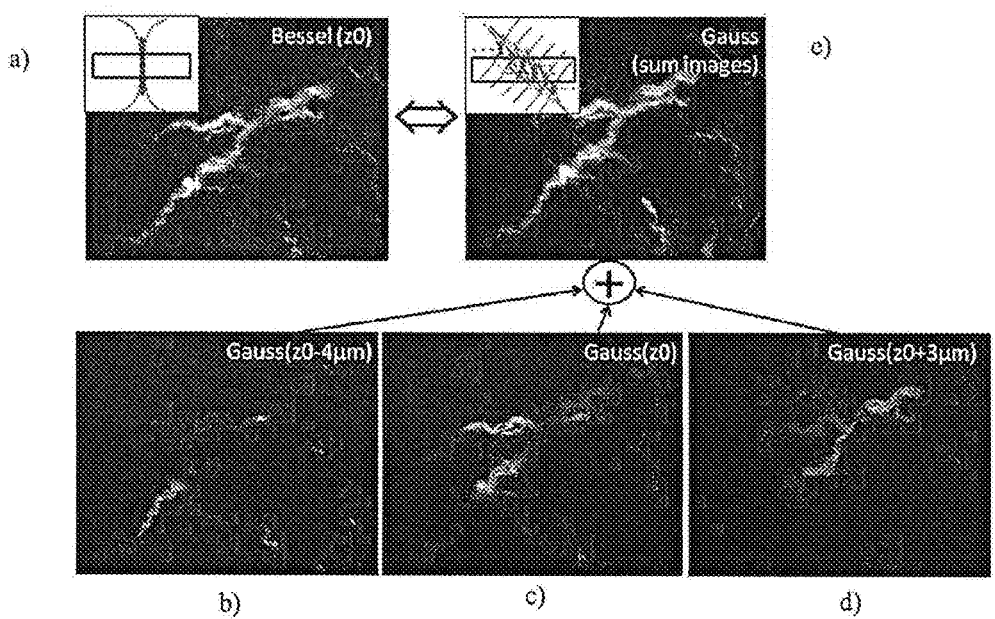
FIG. 4 shows several images comparing an image obtained from a single acquisition with a Bessel beam in the device according to the invention and an image obtained from several acquisitions at different depths with a Gaussian beam.

With reference to FIG. 4, SHG microscopy images of a 15 µm thick histology slide of mouse liver fibrosis can be seen. The excitation is performed either with a Bessel beam produced with an axicon according to the principle shown in FIG. 3b, see image 4a; or with Gaussian beam according to the principle shown in FIG. 3a, see images 4b to 4d assembled in order to obtain a final image 4e. The image 4a obtained with the Bessel beam reveals the collagen fibres present over the entire thickness of the slide, unlike the images 4b to 4e obtained with a Gaussian beam.

Generally, the invention can serve for rapid measurement of any source of contrast in multiphoton microscopy on thin or semi-thick specimens (typically from around a micron to several hundred micrometers). The coherent signals used (SHG, THG, CARS, SRS, FWM type), emitted mainly forwards, are detected directly on a transmission path, or they are detected on a reflection path, either directly via backscattering and retroreflections from the specimen, or by using a reflecting mirror. The non-coherent signals (2PEF, 3PEF) can be detected equally well via a reflection or a transmission path. The acquisition of coherent signals can be combined with the acquisition of the 2PEF/3PEF signals in order to count the cells, for example by using a commonly-used fluorescent marker such as DAPI (Di-Amidino-Phenyl-Indol), for imaging the morphology of the tissue or for visualizing other molecules or structures of interest. This fluorescence can result from immunochemical or histological marking, genetic modifications (fluorescent protein fusions) or endogenous chromophores. Generally, several coherent and incoherent signals can be detected simultaneously in order to locate and quantify simultaneously various components of interest of the tissue, for example (i) the location and quantification of the fibrillar collagen by SHG and of the lipid content by THG, CARS, SRS or FWM microscopy, or (ii) the location and quantification of the fibrillar collagen by SHG and of certain cell types by the 2PEF signal after suitable immunomarking.

In other words, the invention takes advantage of a multiphoton slide scanner, i.e. of an automated device for imaging histology slides over large areas of interest. In this device, the laser beam sweeping can be combined with sweeping by the slide support or entirely replaced thereby. In this case, the stage supporting the slides is finely swept (with a sub-micrometric pitch) over an amplitude of a few centimeters. In this implementation, the invention is applied to paraffin slides or to cryosections whether fixed or not, between slide and cover-glass. Passing from one type of specimen to another (presence of paraffin or not, presence or absence of cover-glass, different thickness of section, etc.) corresponds to different adjustments of the beam shapings used, which can be automated. The loading and course alignment of the slides parallel to the focal plane can also be automated.

With respect to the conventional multiphoton devices, the device according to the present invention comprises at least the following advantages: rapidity of the quantitative measurements, elimination of the problems linked to defects of flatness and horizontality of thin sections.

With respect to the conventional slide scanners, the device according to the present invention comprises at least the following advantages: specificity and high contrast of the nonlinear scatterers compared to histological stains, improved reproducibility due to the absence of marking.

Of course, the invention is not limited to the examples which have just been described and numerous adjustments can be made to these examples without exceeding the scope of the invention.

The invention claimed is:

1. A nonlinear optical microscope comprising:
a source of a pulsed laser beam;
a motorized stage of histology slide scanner assembly, wherein said stage is configured to carry a specimen;
detection means for collecting coherent and non-coherent signals originating from the specimen,
sweeping means for sweeping the laser beam onto the specimen;
a spatial light modulator configured for modulating a spatial profile of the pulsed laser beam; and
an objective configured for guiding the modulated beam towards the slide,
wherein the spatial light modulator is configured to modulate at least one of an intensity and a phase of the pulsed laser beam on a rear pupil of the objective so as to produce a beam that is axially extended and confined in one or two lateral directions after focusing by the objective.

2. The microscope according to claim 1, wherein the modulated beam is a zero-order Bessel beam produced in the form of an annular intensity distribution on the rear pupil of the objective.

3. The microscope according to claim 1, wherein the slide scanner assembly comprises:
a source of white light;
a condenser for guiding the white light towards the slide; and
a camera for producing an image from the white light originating from the slide.

4. The microscope according to claim 1, wherein the detection means comprises a condenser and a detector arranged downstream of the slide with respect to the propagation of the pulsed laser beam so as to detect transmission signals.

5. The microscope according to claim 1, wherein the detection means comprises a detector arranged so as to detect signals reflected from the slide.

6. The microscope according to claim 1, wherein the objective and the condenser are respectively arranged on either side of the slide.

7. The microscope according to claim 1, wherein the objective has a numerical aperture above 0.5.

8. The microscope according to claim 1, wherein the pulsed laser beam is a femtosecond pulse train.

9. The microscope according to claim 1, wherein the pulsed laser beam has a repetition rate greater than approximately ten MHz with a power of several hundred milliwatts.

10. The microscope according to claim 1, wherein the spatial light modulator comprises an element selected from: an axicon; a diffractive element; a liquid crystal modulator, and a modulable liquid lens.

11. A method for quantitative imaging of collagen with the microscope according to claim 1, wherein the imaging is based on an intrinsic second harmonic generation (SHG) signal of fibrillar collagen.

12. A method for quantitative imaging of the lipid content of a tissue with the microscope according to claim 1, wherein the imaging is based on a signal of the third harmonic generation (THG),
Coherent Anti-Stokes Raman scattering (CARS), stimulated Raman scattering (SRS) and/or four-wave mixing (FWM) type.

13. A method for cellular or extra-cellular quantitative imaging with the microscope according to claim 1, wherein the imaging is based on a two- or three-photon excited fluorescence signal.

* * * * *